United States Patent [19]

Isermann et al.

[11] 4,078,054

[45] Mar. 7, 1978

[54] SUN SCREEN COMPOSITIONS OF UNSATURATED ESTERS OF P-DIMETHYLAMINOBENZOIC ACID

[75] Inventors: Howard P. Isermann, West Orange; Joseph P. Ciaudelli, Ramsey, both of N.J.

[73] Assignee: Van Dyk & Company, Incorporated, Belleville, N.J.

[21] Appl. No.: 715,064

[22] Filed: Aug. 17, 1976

[51] Int. Cl.$^2$ .................. A61K 7/44; C07C 101/62
[52] U.S. Cl. ............................. 424/60; 560/19
[58] Field of Search ............. 424/60, 310; 260/471 R

[56] References Cited

U.S. PATENT DOCUMENTS

| | | | |
|---|---|---|---|
| 2,202,865 | 6/1940 | Piggott et al. | 260/471 R |
| 3,403,207 | 9/1968 | Kreps et al. | 424/60 |

OTHER PUBLICATIONS

Chem. Abs., 1961, vol. 55, pp. 2929i.

*Primary Examiner*—Dale R. Ore

[57] ABSTRACT

Compositions containing esters of an unsaturated monohydric alcohol, having from 3 to 10 carbon atoms, of p-dimethylaminobenzoic acid are very effective in controlling sunburn and skin tanning. These novel esters from $C_3$–$C_{10}$ alcohols, which have high "K" values as described, are particularly useful.

8 Claims, No Drawings

SUN SCREEN COMPOSITIONS OF UNSATURATED ESTERS OF P-DIMETHYLAMINOBENZOIC ACID

FIELD OF THE INVENTION

There is an ever increasing need for improved sun screen compositions which while permitting skin tanning help prevent sunburn. This invention provides novel compositions of high efficiency for the purpose.

Extensive studies have been made of the ultraviolet radiation of sunlight and skylight reaching the surface of the earth and the effects of such radiation on the human skin. It has been established that the radiation between 2900 AU and 3150 AU produces substantially all of the burning, or erythemal energy, and a substantial portion of the tanning energy, while the between 3150 AU and 4000 AU promotes incident tanning. The differing intensities and the erythemal and tanning effectiveness of the various wave lengths within these ranges have been established and methods have been determined for calculating accurately their effects on normal untanned skin.

Approximately 76% of the physiological tanning potential of sunlight is found in the ultraviolet range between 2900 AU and 3150 AU, the so-called erythema area; the balance is found in the range between 3150 AU and 4000 AU, the so-called tanning area. The erythemal limitations necessarily control the amount of tanning which may be obtained from ultraviolet in the erythemal area, but there is no limitation on the availability of tanning from the ultraviolet in the incident tanning area since it has no appreciable erythemal effect. Thus, it is apparent that ultraviolet screens can be utilized to furnish any desired amount of protection and/or tanning, by the adjustment of the percentage of such screen used. However, other characteristics of an ultraviolet absorbing screen determine whether it is a commercially practical, all purpose, sun screen for human use: solubility; having sufficiently low melting points so as to be liquid at skin temperatures; and stability.

For human application, ultraviolet screens are incorporated in various cosmetic oil carriers, oily solutions, oil lotions, and creams. Additionally, a material such as dihydroxyacetone may be incorporated in the medium to provide an artificial "tanning" with ultraviolet protection, i.e. pigmentation of the skin which resembles natural melanin pigmentation in appearance only.

Therefore, a practical, all-purpose ultraviolet or sun screen should:

Provide high screening efficiency in the erythemal area coupled with high transmission of incident tanning energy;

Be capable of being readily incorporated in the various oil media used to apply them to human skin, and remain stable, effective and cosmetically acceptable therein under all conditions normally encountered in commercial use;

Be liquid at skin temperature and form a thin, continuous, long-lasting protective film on the skin;

Be resistant to oxidation by air and stable on exposure to both ultraviolet and visible radiation under all normal conditions of storage, application and use.

DESCRIPTION OF THE PRIOR ART

Lower saturated alcohol esters of p-dimethylaminobenzoic acid are known to be good UV absorbers, but typically their insolubility in oil cosmetic carriers, and solid state at normal skin temperatures, rendered them unsatisfactory for sun screen use. Higher saturated alcohol esters overcome these deficiencies, i.e. U.S. Pat. No. 3,403,207, but with some dilution of the chromophore group by the additional molecular weight involved, which in no way contributes to the UV absorption characteristics of the molecule.

SUMMARY OF THE INVENTION

It has now been found that esters of an unsaturated monohydric alcohol having from 3 to 10 carbon atoms of p-dimethylaminobenzoic acid are extremely effective sun screen agents.

DISCUSSION OF PREFERRED EMBODIMENTS

The materials of this invention as stated are esters of an unsaturated monohydric alcohol, having from 3 to 10 carbon atoms, of p-dimethylaminobenzoic acid. Those esters from $C_3$–$C_5$ alcohols are particularly useful. Especially effective and useful is the allyl unsaturated $C_3$ ester as it is liquid at skin temperatures and soluble in mineral oils. By contrast the saturated $C_3$ propyl ester is solid at skin temperatures and insoluble in mineral oils.

The materials of this invention are further characterized in being relatively miscible in cosmetic oil carriers at various atmospheric temperatures, e.g. allyl p-dimethylaminobenzoate is miscible with mineral oil, vegetable oil and isopropyl myristate as a 5% solution at room temperature, and having a sufficiently low melting point as to be liquid at skin temperatures, i.e. having a maximum m.p. of about 40° C. Thus, determining the esters that qualify has been empiric as is shown.

Esters of p-dimethylaminobenzoic acid can be prepared by several methods. U.S. Pat. No. 2,202,865 describes the preparation of esters by reacting p-dimethylaminobenzoyl chloride with alcohols. Another method is by reacting an alkali salt of p-dimethylaminobenzoic acid with an alkene halide. Either method can be used but the latter is preferred. For example, if allyl chloride is added to sodium p-dimethylaminobenzoate in a suitable solvent such as dimethylformamide using a quaternary ammonium salt catalyst, allyl-p-dimethylaminobenzoate is obtained in yield of about 60%.

The cosmetic oil carriers are those known to the trade, e.g. mineral, vegetable and animal oils, and isopropyl myristate.

The active ester component is utilized in an amount sufficient to provide the desired protection up to the limit of solubility of the carrier. Compounds which have the property of absorbing ultraviolet radiation between 2900 and 3150 AU are candidates as sunscreening agents. The effectiveness of a sunscreening agent can be determined by dividing the absorbance at the maximum peak between 2900 and 3150 by the concentration in grams per liter. This is known as the "K" value of a sunscreening agent. The higher the "K" value, the better the sunscreening ability and the lower the amount of material needed for protection from erythemal rays of the sun. In other words, from the "K" value the amount of sunscreening agent necessary for protection of the sun ultraviolet radiation can be determined and used in any cosmetically acceptable base preparation. Typical ranges employed in the base are 1 to 8 wt.%.

This invention and properties of the active materials will be better understood by reference to the following examples.

EXAMPLE 1

The following data characterizes unsaturated esters of interest. The various alcohols are listed in ascending carbon content.

| Compound | $\lambda m\mu$* | "K" Value |
| --- | --- | --- |
| Allyl | 307 | 138 |
| 1-Penten-3-yl | 308 | 123 |
| 4-Penten-2-yl | 308 | 115 |
| 3-Penten-2-yl | 308 | 102 |
| 4-Penten-1-yl | 308 | 116 |
| 1-Octen-3-yl | 308 | 100 |
| 3-Octyn-1-yl | 308 | 99 |
| Geranyl | 308 | 85 |
| Citronellyl | 304 | 78 |

*Maximum absorbtion wave length

An increase in the molecular weight of the esters decreases the "K" value for the sunscreening agent. In these cases an increase in the weight amount of sunscreen would compensate for the lower "K" value. In other words, twice the amount of citronellyl-p-dimethylaminobenzoate would, in general, be needed to give the same sunscreening protection as allyl-p-dimethylaminobenzoate.

EXAMPLE 2

The following are illustrative cosmetic preparations utilizing the sunscreening agents which have been described hereinabove. All parts are listed by weight except where otherwise indicated.

| Sunblock Cream | |
| --- | --- |
| Stearic Acid | 3.5 |
| Isopropyl Myristate | 5.0 |
| Allyl-p-dimethylaminobenzoate | 2.5 |
| Myristyl Myristate | 3.5 |
| Glycol Amido Stearate | 4.5 |
| 4% Veegum in Water | 25.0 |
| Triethanolamine | 1.0 |
| Carbowax 400 | 5.0 |
| Water | 49.8 |
| Preservative | 0.2 |

EXAMPLE 3

| Sun Tan Cream Lotion | |
| --- | --- |
| Stearic Acid | 3.0 |
| Lanolin, U.S.P. Anhydrous | 1.0 |
| Ethylene Glycol Monostearate, Self Emulsifying | 10.0 |
| Mineral Oil 65/75 | 6.0 |
| Cetyl Alcohol | 1.0 |
| Polyoxyalkylene Oleate-Laurate | 3.0 |
| Coconut Oil | 2.0 |
| Cocoa Butter | 1.0 |
| Triethanolamine | 2.0 |
| Glycerine USP | 5.0 |
| 4-Penten-2-yl-p-dimethylaminobenzoate | 1.2 |
| Water | 64.8 |
| Perfume and Color | as much as suffices |

EXAMPLE 4

| Waterproof Sun Gel | |
| --- | --- |
| White Petrolatum | 71.6 |
| 3-Octynyl-p-dimethylaminobenzoate | 1.2 |
| Calcium Stearate | 5.0 |
| Butyl Stearate | 5.0 |
| Stearyl Alcohol | 5.0 |
| Preservative | 0.2 |
| Mineral Oil 345/355 | 10.0 |
| Beeswax USP | 2.0 |
| Perfume, Color | as much as suffices |

The advantages of this invention will be apparent to the skilled in the art. Improved, highly effective, novel sun screen compositions are made available.

It will be understood that this invention is not limited to the specific examples which have been offered as particular embodiments, and that modifications can be made without departing from the spirit thereof.

What is claimed is:

1. A composition adapted for application to the human skin comprising a cosmetic oil carrier containing distributed therein from an effective amount to provide substantial protection against erythemal radiation up to the limit of solubility therein of an ester of an unsaturated monohydric alcohol, having from 3 to 10 carbon atoms, of p-dimethylaminobenzoic acid, said ester having a sufficiently low melting point as to be liquid at skin temperatures, and being miscible in said carrier at said temperatures.

2. The composition of claim 1 in which the alcohol is allyl.

3. The composition of claim 1 in which the alcohol is a pentenyl.

4. The composition of claim 1 in which the alcohol is 1-octen-3-yl.

5. An ester of an unsaturated monohydric alcohol, having from 3 to 10 carbon atoms, of p-dimethylaminobenzoic acid.

6. The chemical of claim 5 in which the alcohol is allyl.

7. The chemical of claim 5 in which the alcohol is a pentenyl.

8. The chemical of claim 5 in which the alcohol is 1-octen-3-yl.

* * * * *